United States Patent
Olbert et al.

(10) Patent No.: US 7,226,567 B1
(45) Date of Patent: Jun. 5, 2007

(54) MULTI-TUBE FIXED-BED REACTOR, ESPECIALLY FOR CATALYTIC GAS PHASE REACTIONS

(75) Inventors: Gerhard Olbert, Dossenheim (DE); Franz Corr, Ludwigshafen (DE); Peter Reuter, Mannheim (DE); Ludwig Wambach, Schwetzingen (DE); Ulrich Hammon, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/936,354

(22) PCT Filed: Mar. 15, 2000

(86) PCT No.: PCT/EP00/02304

§ 371 (c)(1),
(2), (4) Date: Sep. 11, 2001

(87) PCT Pub. No.: WO00/54877

PCT Pub. Date: Sep. 21, 2000

(30) Foreign Application Priority Data

Mar. 16, 1999 (DE) ................. 199 12 735
Nov. 23, 1999 (DE) ................. 199 56 329

(51) Int. Cl.
*B01J 8/06* (2006.01)
(52) U.S. Cl. .................................. 422/197
(58) Field of Classification Search ............. 422/188, 422/196, 197
See application file for complete search history.

(56) References Cited

U.S. PATENT DOCUMENTS

| | | | |
|---|---|---|---|
| 3,566,961 A | 3/1971 | Friedrich et al. ........... 165/159 |
| 3,910,768 A * | 10/1975 | Woebcke et al. ........... 422/197 |
| 4,398,595 A | 8/1983 | Small ........................ 165/109 |
| 4,505,879 A | 3/1985 | Lhonore et al. ............ 422/197 |
| 4,894,205 A * | 1/1990 | Westerman et al. ........ 422/197 |
| 5,227,556 A * | 7/1993 | Benton et al. .............. 585/323 |
| 5,723,094 A * | 3/1998 | Sunavala .................... 422/197 |
| 5,730,843 A * | 3/1998 | Groten et al. ............... 202/158 |
| 5,821,390 A * | 10/1998 | Ruppel et al. .............. 568/470 |
| 6,191,332 B1 * | 2/2001 | Duee et al. ................. 585/654 |
| 6,296,679 B1 * | 10/2001 | Kato ........................ 48/197 R |
| 6,296,814 B1 * | 10/2001 | Bonk et al. ................ 422/196 |

FOREIGN PATENT DOCUMENTS

DE          23 30 765         1/1980

* cited by examiner

Primary Examiner—Kevin P. Kerns
(74) Attorney, Agent, or Firm—Novak Druce & Quigg, LLP

(57) ABSTRACT

A multitube fixed bed reactor and the use of such a reactor for carrying out catalytic gas-phase reactions, in particular for carrying out exothermic and endothermic catalytic gas-phase reactions such as the preparation of phthalic anhydride (PA), acrylic acid, methacrylic acid (MAA), acrolein, maleic anhydride (MA), glyoxal, phosgene, hydrocyanic acid or vinyl formamide (VFA). In a relatively large multitube reactor in which a large amount of heat of reaction is generated owing to the numerous catalyst tubes (17) and has to be removed, it is proposed that the ratio of tube spacing t to external tube diameter $d_a$ be made dependent on the reactor diameter or on the external tube bundle diameter $d_{RBa}$. At an external diameter of the catalyst tube bundle (18) of more than 4 meters, a ratio of tube spacing d to external tube diameter $d_a$ of at least 1.3 is preferred.

11 Claims, 4 Drawing Sheets

MULTI-TUBE FIXED-BED REACTOR, ESPECIALLY FOR CATALYTIC GAS PHASE REACTIONS

The present invention relates to a multitube fixed bed reactor and the use of such a reactor for carrying out catalytic gas-phase reactions, in particular for carrying out exothermic and endothermic catalytic gas-phase reactions such as the preparation of phthalic anhydride (PA), acrylic acid (AA), methacrylic acid (MAA), acrolein, maleic anhydride (MA), glyoxal, phosgene, hydrocyanic acid or vinyl formamide (VFA).

BACKGROUND OF THE INVENTION

In the chemical industry, multitube reactors are usually used for carrying out catalytic gas-phase reactions over fixed-bed catalysts.

Multitube reactors usually comprise a catalyst tube bundle made up of numerous parallel catalyst tubes and arranged within an outer wall. The catalyst tubes, which usually contain supported or unsupported catalysts, have their open ends fixed so as to form a seal to tube plates and each of them opens into a cap connected to the outer wall at the upper or lower end. Apart from supported catalysts, the catalyst tubes may, alternatively or in addition, contain shell catalysts, solid catalysts or ordered packings of catalyst material arranged like a static mixer. It is also possible to coat the inner surface of the catalyst tubes with catalyst material. The reaction mixture flowing through the catalyst tubes is fed in and discharged via the caps. A heat transfer medium is circulated through the space located between the uppermost and bottommost tube plates and surrounding the catalyst tubes, which space may be divided by deflecting plates, in order to introduce or remove heat of reaction. For this purpose, the outer wall of the multitube reactor has means for feeding in and discharging the heat transfer medium, usually suitable annular inlet and outlet channels through which the heat transfer medium is circulated by means of suitable pumps. After leaving the multitube reactor, the heat transfer medium is again brought to a prescribed temperature, for example in an external heat exchanger, before it re-enters the reactor. As far as exothermic reactions are concerned, hot cooling may be applied for reactor temperature control as well.

The multitube reactors used in industrial production processes have a diameter of several meters. For economic reasons, as large as possible a number of catalyst tubes is used in the reactor. In the case of a reactor having a diameter of several meters, the number of catalyst tubes is usually in the range from 10,000 to 50,000, preferably in the range of 10.000 to 30.000. In the past, it has been considered important to pack the tubes of industrial multitube reactors as tightly as possible in order to achieve as small as possible a reactor diameter for a maximum number of catalyst tubes. Usually, the tubes are positioned in a triangular arrangement, in most cases in an equilateral triangle. A measure used for the compact arrangement of the catalyst tubes is the ratio of the tube spacing t to the external diameter $d_a$ of a tube. Here, the tube spacing is the distance from the central internal axes of nearest-neighbor catalyst tubes. Known industrial reactors, for instance the reactor described in the examples of DE 44 31 957 A1, have a ratio of tube spacing to external tube diameter of 1.28 or less.

Particularly when carrying out strongly exothermic oxidation reactions, for example the preparation of phthalic anhydride, acrylic acid, methacrylic acid, acrolein, maleic anhydride or glyoxal, precise control of the reaction temperature plays a critical role. In these reactions, a gas mixture is passed through the catalyst tubes which contain a fixed bed of a catalytically active multimetal oxide. For example, multitube reactors are used for preparing phthalic anhydride which is an important intermediate for producing synthetic resins, phthalate plasticizers, phthalocyanine dyes and further fine chemicals. The worldwide production of phthalic anhydride is more than 4,000,000 metric tons per year. Most phthalic anhydride is now produced by gas-phase oxidation of o-xylene using air as oxidant. For this purpose, o-xylene is vaporized, mixed with an excess of air and passed at 340–440° C. over the catalyst present in the catalyst tubes. The catalyst can, for example, comprise a mixture of $V_2O_5$ and $TiO_2$ with promoters on ceramic bodies such as porcelain or SiC spheres or rings. Typical dimensions of these ceramic bodies are about 6 mm×6 mm or 8 mm×6 mm, respectively. In this process, the o-xylene is oxidized to phthalic anhydride with a selectivity of 78–80%. With an enthalpy of reaction of about −1110 kJ/mol, the oxidation is strongly exothermic.

Suitable heat transfer media are, in particular, fluid heat transfer media which are liquid in the preferred reaction temperature range from 250° C. to 500° C., preferably from 250° C. to 380° C. For example, the use of melts of salts is particularly useful, such as a melt of a mixture of potassium nitrate, sodium nitrite and sodium nitrate, which melt is particularly preferred in PA synthesis.

The reaction conditions, in particular reactor temperature control, require particular attention for a number of reasons: the large number of tubes in the reactor makes it necessary for the gas mixture flowing into all tubes over the entire cross section to be the same and constant over time, so that the reaction proceeds at the same rate in all tubes and does not proceed particularly quickly in a few preferred tubes. However, the high enthalpy of reaction liberated can, in particular, lead to the catalyst sintering or melting or becoming inactive in individual tubes in the case of deviations from the prescribed temperature range. This is associated with considerable risks for the plant. Inhomogeneities in the throughput also lead to different reaction conditions in the tubes. This results in formation of increased amounts of by-products which reduce the yield and have to be separated from the resulting phthalic anhydride in later purification steps and have to be disposed of. In the gas-phase oxidation, the reaction temperature goes through a maximum along a catalyst tube in the flow direction and this maximum is referred to as a hot spot. Such a hot spot is desirable in principle but problems occur if the hot spot temperature is too high, since this leads both to a reduced catalyst life and to a decrease in the selectivity of the reaction.

In principle, effective reactor temperature control therefore has the task of reducing temperature inhomogeneities over the cross section of the reactor and to prevent the occurrence of undesirably high hot spots.

In the case of previously known reactors, which generally have a very small ratio of tube spacing to external tube diameter, effective reactor temperature control was possible to only a limited extent. Particularly in the case of cylindrical reactor geometries, a transverse stream of the heat transfer medium is passed from a region outside the catalyst tube bundle to an inner space of the reactor which is free of catalyst tubes, or vice versa. This leads to a large pressure drop and thus to a restricted flow of heat transfer medium. In the past, one was therefore forced to use high-performance and consequently very expensive pumping facilities for conveying the heat transfer medium.

SUMMARY OF THE INVENTION

It is an object of the present invention to provide a reactor which makes possible a more uniform temperature distribution over the radial reactor cross section and also substantially reduces excessively high heat transfer medium hot spots.

We have found that this object is achieved by the multitube reactor as described herein. According to the present invention, it is proposed that in the case of relatively large reactors in which a large amount of heat of reaction is generated owing to the numerous catalyst tubes and has to be removed, the ratio of tube spacing t to external tube diameter $d_a$ be made dependent on the reactor diameter or on the external tube bundle diameter $d_{RBa}$. In particular, the present invention proposes providing a ratio of tube spacing t to external tube diameter $d_a$ of at least 1.3. Preferably, the catalyst tubes are arranged such that three adjacent tubes form a triangle, preferably a equilateral triangle. In this case, tube spacing t is equal to the length of the sides of the triangle.

The present invention accordingly provides a multitube reactor which has a catalyst tube bundle comprising numerous parallel catalyst tubes arranged within an outer wall and has means for introducing and discharging a heat transfer medium flowing around the catalyst tubes, wherein the ratio $t/d_a$ of tube spacing t to external tube diameter $d_a$ of a catalyst tube is at least 1.3.

The multitube reactor of the present invention has numerous advantages.

Increasing the ratio of tube spacing to external tube diameter allows higher heat transfer medium flows at a given pump power and thus leads to a more uniform temperature over the cross section and to a reduction in the heat transfer medium hot spot.

Surprisingly, it is found that it is possible to increase the entry temperature of the heat transfer medium without exceeding the maximum permissible exit temperature of the heat transfer medium. This leads to an improved selectivity of the reaction an thus to an increase in the yield. The reactor capacity increases by up to 2%.

The reduction in the heat transfer medium hot spot leads to greater operational safety since the danger of ignition of the reaction mixture is greatly reduced.

Especially when using the novel multitube reactor in PA synthesis, it is found that a spacing ratio of more than 1.3 allows a significantly higher loading of the inflowing gas mixture with o-xylene.

The tube spacing is only slightly greater than that in the prior art and also leads to only a slight increase in the reactor diameter. Interestingly, it is found that this slight increase in the dimensions at a given pump power allows an almost doubled heat transfer medium flow.

According to the present invention, it is also proposed that the ratio $t/d_a$ of tube spacing to external diameter of a catalyst tube be increased with increasing external diameter $d_{RBa}$ of the catalyst tube bundle. This makes it possible to take account of the heat of reaction to be introduced or removed, which becomes very high with a rising external tube bundle diameter and thus a greatly increasing number of tubes.

The spacing ratio of more than 1.3 proposed according to the present invention is particularly advantageously employed in large reactors. In a first preferred embodiment, the catalyst tube bundle has an essentially circular cross section having an external diameter $d_{RBa}$ of more than 4 m. Such a catalyst tube bundle usually has a tube-free central region by which the heat transfer medium flowing radially past the catalyst tubes can flow away in an axial direction.

In this embodiment, the ratio $t/d_a$ of tube spacing to external diameter of a catalyst tube is particularly preferably in the range from 1.3 to 1.6 for catalyst tube bundle diameters of from 4 m to 12 m and is most preferably in the range from 1.3 to 1.5 for catalyst tube bundle diameters of from 4 m to 10 m.

Multitube reactors having such diameters generally have from 10,000 to 50,000, preferably from 10.000 to 30.000 catalyst tubes.

However, the invention is not restricted to reactors having cylindrical catalyst tube bundles. If, for example, catalyst tube bundles having a rectangular cross section or a circular cross section with end segments free of catalyst tubes are employed, the ratio of tube spacing to external tube diameter is preferably dependent on the depth $d_{RBt}$ of the tube bundle through which the heat transfer medium flows transversely. At a spacing ratio of 1.3 according to the present invention, the catalyst tube bundle preferably has an essentially rectangular cross section with a tube bundle depth measured parallel to the flow direction of the heat transfer medium of at least 1.3 m.

The depth $d_{RBt}$ of the catalyst tube bundle is advantageously from 1.3 m to 4 m, in which case the ratio $t/d_a$ of tube spacing t to the external diameter $d_a$ of a catalyst tube is then in the range from more than 1.3 to 1.6.

The catalyst tubes are usually made of ferritic steel and have a typical wall thickness of from 1 to 3 mm. Their internal diameter is generally from 20 to 70 mm, preferably from 20 to 35 mm. The typical length of the catalyst tubes and thus the length of the cylindrical region of the reactor is in the range from 1.5 to 7 m.

In the case of catalyst tube bundles having an essentially rectangular cross section, the ratio of cross-sectional depth $d_{RBt}$ to cross-sectional length of the bundle is preferably from 1:1 to 1:10, particularly preferably from 1:1.5 to 1:4.

The reactor of the present invention enables flows of the heat transfer medium, for instance a salt melt, of from 10,000 to 20,000 $m^3$ per hour to be achieved.

A reduction in the reaction-related hot spot in the catalyst tube increases the life of the catalyst and also improves the selectivity of the reaction. In particular, the lengthening of the catalyst life represents an important advantage of the reactor of the present invention, since the replacement of the catalyst material required after a certain operating time is associated with high costs and long downtimes of the reactor.

Often, the reaction in the tubes of the reactor is controlled by the catalyst load. It is e.g. possible to use a structured bed with two different catalysts which provide for different reaction conditions along a catalyst tube. According to another preferred embodiment of the multitube reactor of the invention, the interior of the reactor is, in the longitudinal direction of the tubes, divided into at least two zones, with a flow of heat transfer medium of different temperature being provided in each zone, respectively. On the one hand, his measure provides for a further possibility to control the reaction by thermostatting the catalyst at different temperatures. On the other hand, in some processes it allows for using only a singe type of catalyst for filling the tubes, while control of the reaction being provided only by using two or more, preferably up to five zones of different temperature. Preferably, the temperature difference between adjacent zones is up to 60° C., preferably up to 40° C. Different zones are separated from each other by means of tube sheets which are arranged essentially horizontally inside the reactor and which are provided with passages for the catalyst tubes.

The present invention also provides for the use of a multitube reactor according to the present invention for carrying out catalytic gas-phase reactions.

In particular, the present invention provides for the use of a multitube reactor according to the present invention for carrying out oxidation reactions, in particular for the preparation of phthalic anhydride, maleic anhydride, acrylic acid, acrolein, methacrylic acid, glyoxal, phosgene, hydrocyanic acid or vinyl formamide. Such processes using multitube reactors containing fixed-bed catalysts are known (cf., for example, Ullmann's Encyclopedia of Industrial Chemistry, 5th Edition, Volume B4, Table 7 on page 103, with further references).

In the following, the invention is described in more detail with reference to the preferred illustrated embodiments shown in the attached drawing. The preparation of phthalic anhydride mentioned below is presented purely as an example of the use of the reactor of the present invention in oxidative gas-phase reactions and does not imply any restriction of the invention to this application.

DESCRIPTION OF THE PREFERRED EMBODIMENTS

Figure 1:
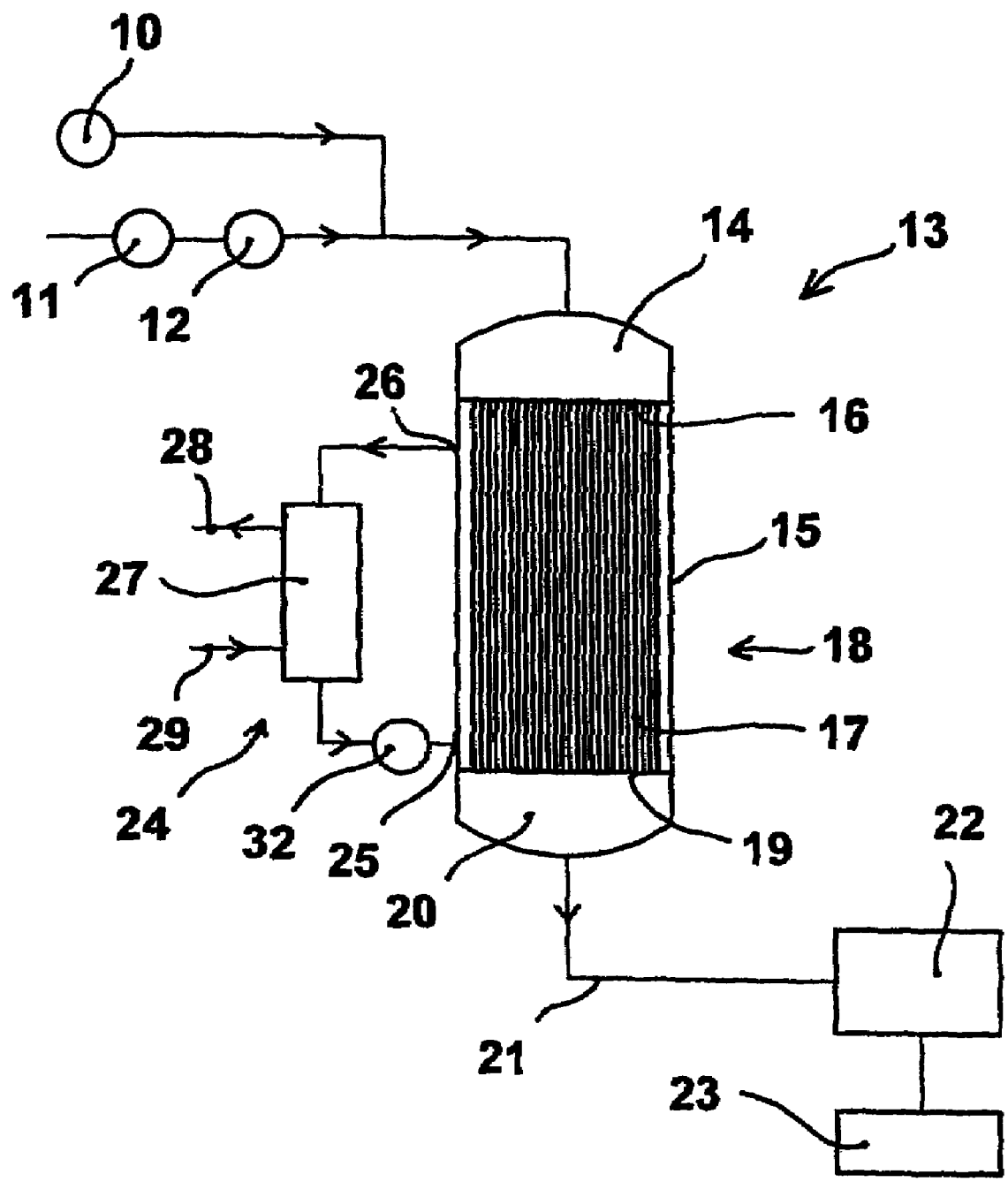
FIG. 1 schematically shows a reactor according to the present invention integrated into a plant for producing phthalic anhydride.

In FIG. 1, it is possible to see a schematic outline of a plant for preparing phthalic anhydride. A detailed description of the process may be found, for example, in Ullmann's Encyclopedia of Industrial Chemistry, 5th Edition, Vol. 20A, p. 181 ff.

o-Xylene or naphthalene is vaporized in the vaporizer 10 and mixed with an excess of air supplied via blower 11 and heated to from about 120 to 300° C. in a heater 12. The o-xylene/air mixture goes to the reactor 13 where, in the region of the upper cap 14, it is uniformly distributed over the entire reactor cross section. The upper cap 14 is joined to the cylindrical reactor wall 15 by means of an upper plate 16. The catalyst tubes 17 of the tube bundle 18 open into the plate 16. The top ends of the catalyst tubes 17 are welded to the plate 16 so as to be free of leaks. The catalyst material (not shown) is located in the catalyst tubes 17. The lower ends of the catalyst tubes 17 are welded to a bottom plate 19 so as to be free of leaks and open into a bottom cap 20 of the reactor 13. The o-xylene/air mixture flows through the catalyst tubes and is mostly oxidized to phthalic anhydride.

The hot reaction gas is passed via a line 21 to desublimators or separators 22 where the product is deposited in the form of very fine crystals. The phthalic anhydride is melted off the separators 22 g multitube reactors containing fixed-bed catalysts are known and the pure product is obtained in a subsequent distillation apparatus 23 from the crude phthalic anhydride melted off (as described in Ullmann's Encyclopedia of Industrial Chemistry, 5th Edition, Volume 20A, pages 181 et seq.).

The temperature of the catalyst tube bundle 18 is controlled by means of a heat exchange circuit which is denoted overall by the reference numeral 24. For this purpose, a salt melt of sodium nitrate, sodium nitrite and potassium nitrite is passed into the cylindrical section of the reactor via openings 25 in the wall and is there conveyed longitudinally, transversely, in cocurrent or countercurrent past the catalyst tubes 17 of the tube bundle 18 in order to remove the heat of reaction generated in the oxidation of o-xylene.

The heat transfer medium leaves the reactor via openings 26 in the wall and goes to an external heat exchanger 27 which is brought to the desired reaction temperature, usually in a range from 340 to 440° C., by means of a steam generator (not shown) via circuit 28, 29. The exact choice of reaction temperature depends, in particular, on the catalyst material used and should be kept as constant as possible.

Figure 2:
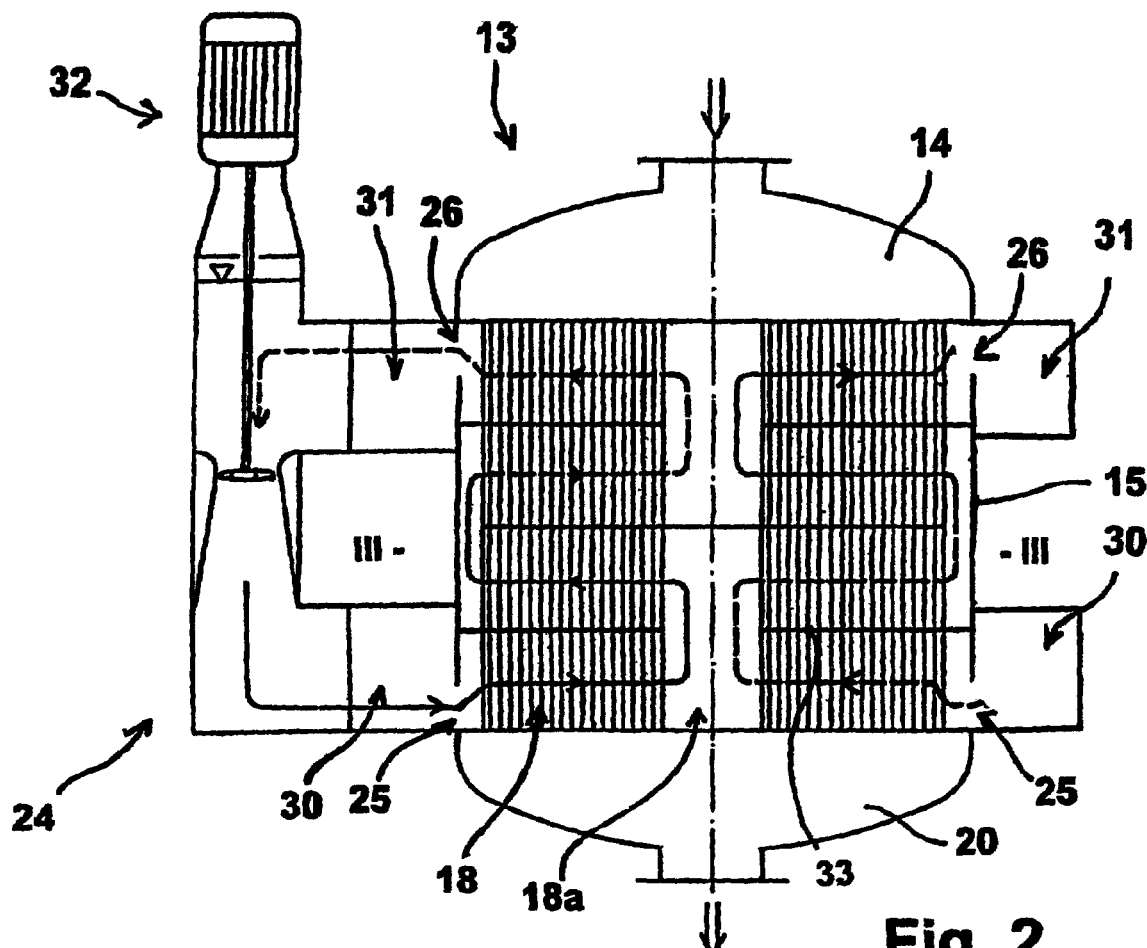
FIG. 2 shows a longitudinal section of a first embodiment of the reactor of the present invention.
Figure 3:
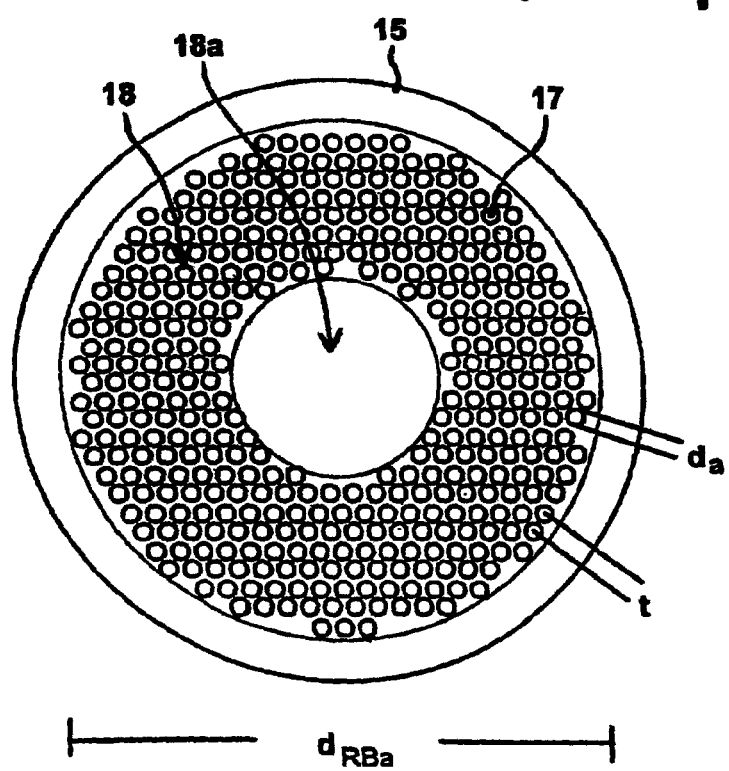
FIG. 3 shows a cross section through the reactor of FIG. 2 along the line III—III.

FIG. 2 shows a first embodiment of the multitube reactor of the present invention in more detail. FIG. 3 shows a section through the reactor of FIG. 2 along the line III—III. Elements which have a comparable function to elements described above in connection with FIG. 1 are denoted by the same reference numerals.

The cylindrical reactor 13 has a vertical catalyst tube bundle 18 having a circular cross section and an external diameter $d_{RBa}$ (cf. FIG. 3). The catalyst tubes 17 are uniformly distributed over an annulus. The central region 18a of the tube bundle 18 is free of catalyst tubes.

The heat transfer medium is introduced into or discharged from the space surrounding the catalyst tubes through openings 25, 26 in the wall via annular lines 30, 31 by means of one or more pumps 32. A meandering flow of the heat transfer medium is achieved by means of deflecting plates 33 arranged in the reactor, but radial flow prevails in the region of the catalyst tubes 17.

Figure 4:
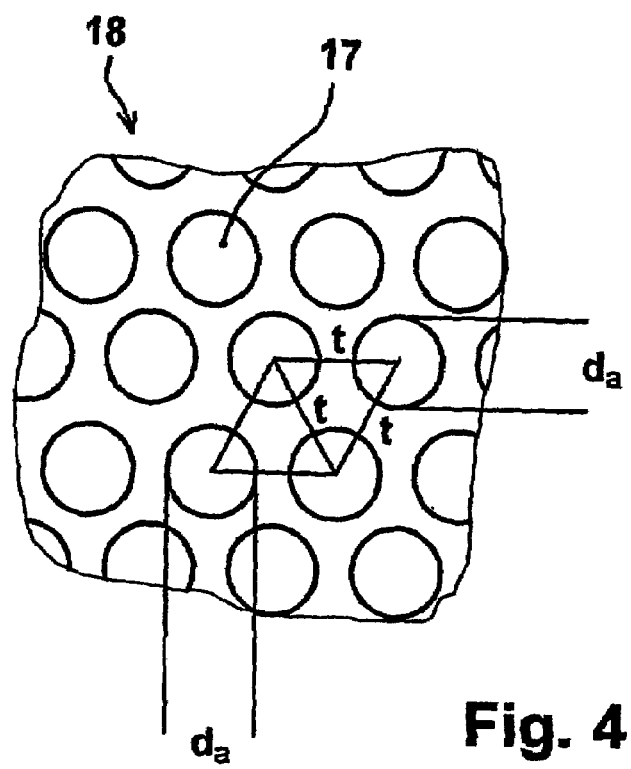
FIG. 4 shows an enlarged view of a section of the reactor of FIG. 3.

In the cross-sectional view of FIGS. 3 and 4, the tube spacing t, the external diameter $d_a$ of a catalyst tube 17 and the external diameter $d_{RBa}$ of the catalyst tube bundle 18 are indicated. It should be noted that the diagram in FIG. 3 (likewise those of FIGS. 6 and 7) is not to scale. In reality, the diameter of the catalyst tubes 17 compared to the external tube bundle diameter is significantly smaller.

To enable the essential parameters of the multitube reactor of the present invention to be seen more clearly, a section of the tube bundle 18 shown in FIG. 3 is depicted on a larger scale in FIG. 4. Especially in FIG. 4 it is shown that three adjacent catalyst tubes form the corners of an equilateral triangle.

Figure 5:
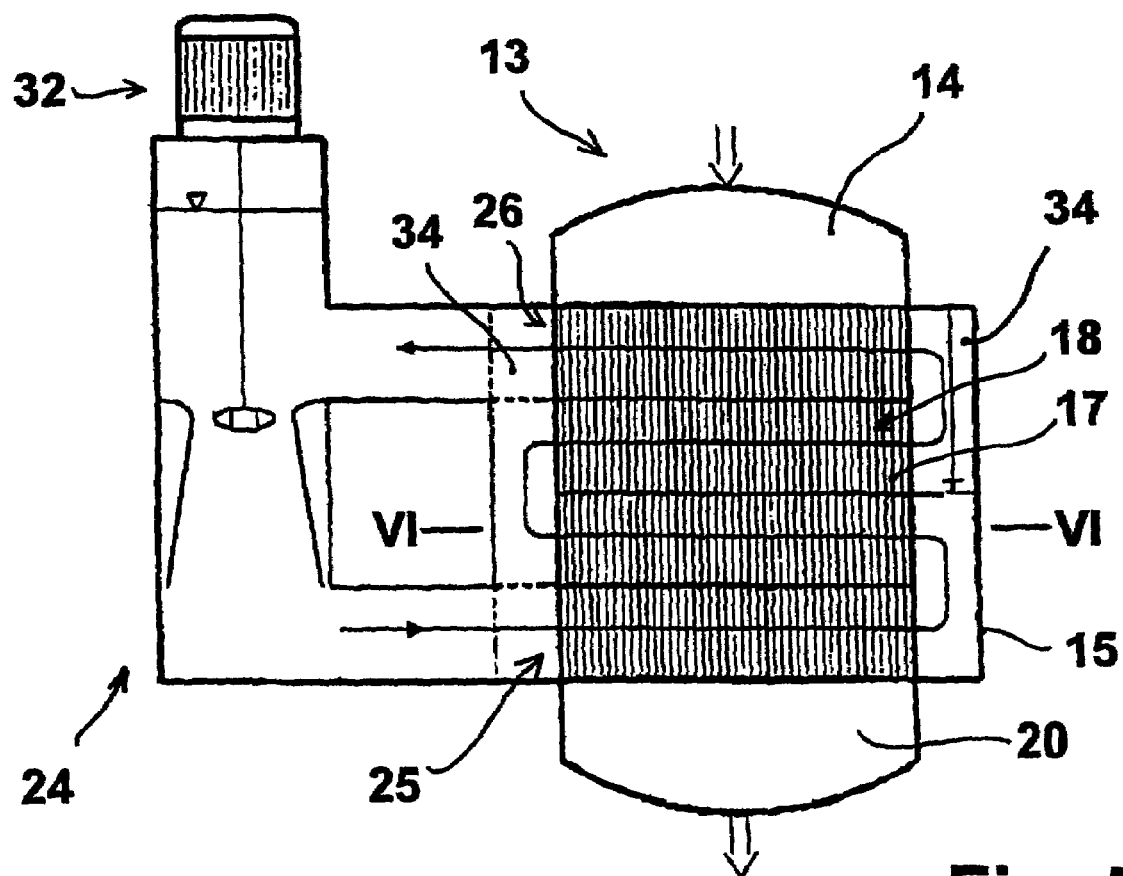
FIG. 5 shows a longitudinal section of a second embodiment of the reactor of the present invention.
Figure 6:
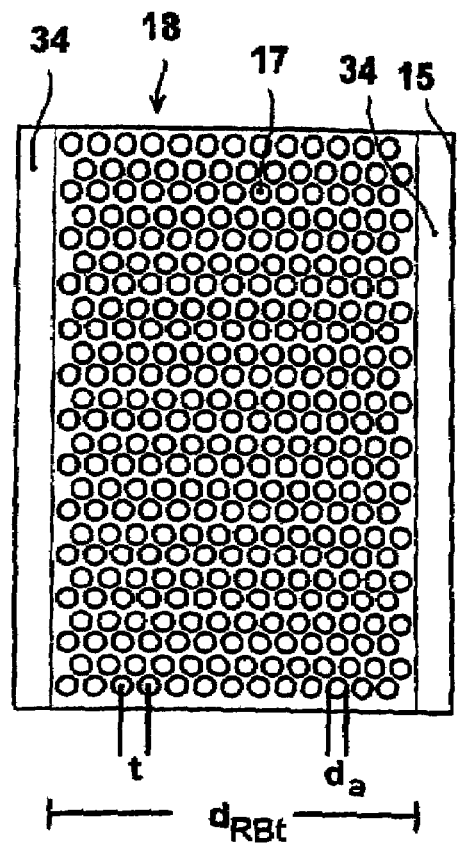
FIG. 6 shows a cross section through the reactor of FIG. 5 along the line VI—VI.
Figure 7:
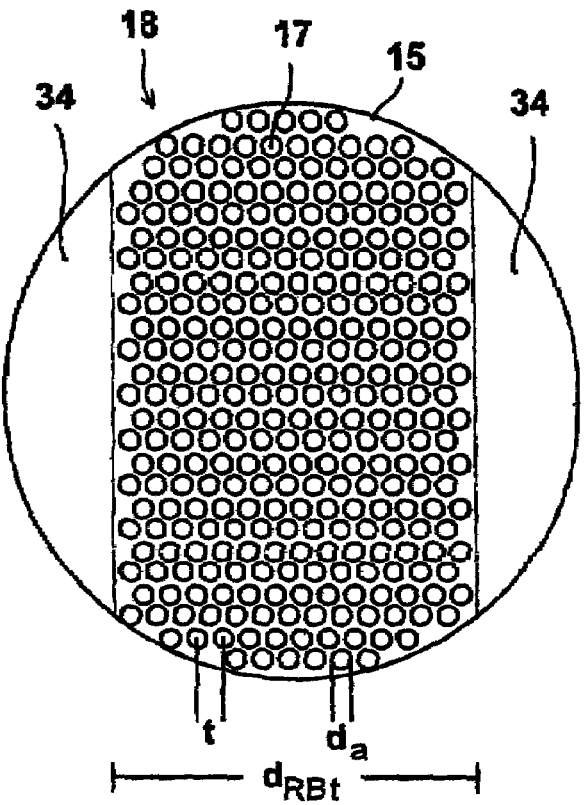
FIG. 7 shows a cross section through a third embodiment of the reactor of the present invention.

The embodiment of the reactor of the present invention shown in FIGS. 5 and 6, and also the variant of FIG. 7, each have a catalyst tube bundle 18 having an essentially rectangular cross section. Such a geometry gives advantages in terms of the transport of heat transfer medium owing to the lower flow resistances, especially in the case of transverse flow cooling.

These advantages are further reinforced by the spacing ratio proposed according to the present invention.

Spaces 34 which are free of catalyst tubes for distributing or collecting the heat transfer medium are provided at broad side faces of the reactor located opposite one another. In the variant of FIG. 6, the reactor wall 15 itself has a rectangular cross section, while the variant of FIG. 7 uses a cylindrical reactor. In the latter case, the essentially rectangular cross section of the catalyst tube bundle 18 is obtained as a result of the segments 34 which are free of catalyst tubes. According to the present invention, the spacing ratio in the case of essentially rectangular catalyst tube bundles is chosen as a function of the depth $d_{RBt}$ of the tube bundle 18 through which transverse flow occurs.

Figure 8:
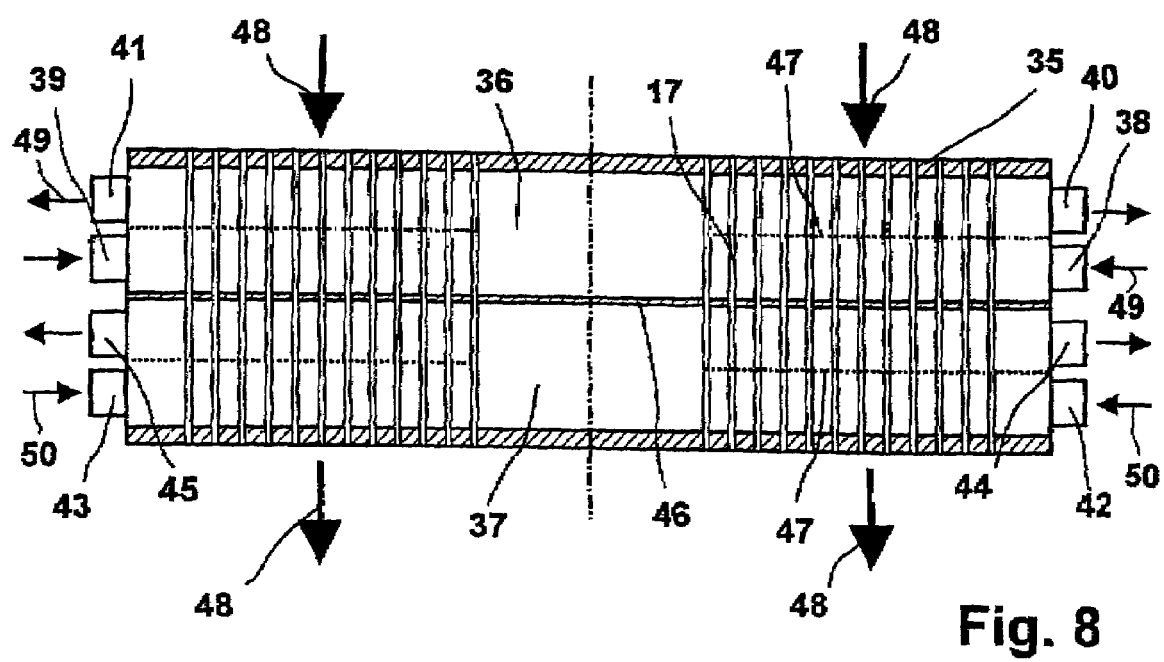
FIG. 8 shows a longitudinal section of a fourth embodiment of the reaction of the present invention.

Finally, FIG. 8 show a schematic longitudinal section of a fourth embodiment of the multitube reactor of the present invention. In this embodiment, reactor 35 is a two-zone reactor which is, in the longitudinal direction of the catalyst tubes 17, divided into two zones 36, 37 maintained at different temperatures. Zones 36 and 37 are supplied by separate heat exchange circuits. In the example depicted, a first salt solution is introduced via fittings 38, 39 into the first zone 36 and withdrawn therefrom via fitting 40, 41. Correspondingly, a second salt solution is introduced via fittings 42, 43 into the second zone and withdrawn therefrom via fittings 44, 45. Both zones 367, 37 are separated from each other by means of a tube sheet 46 having a thickness of 50 mm. The sheet comprises openings through which the catalyst tubes 17 are inserted. After insertion, the tubes are widened hydraulically to some extent so as to provide for a good and largely leak-tight fit of the tubes 17 in tube sheet 46. In each zone baffle plates 47 are provided for guiding the salt melt radially from an outer region to the center of the reactor which is free from catalyst tubes, where the melt is directed upwards to be then again directed to the outer region of the reactor. In FIG. 8, large arrows 48 indicate the flow direction of reaction gases while smaller arrows 49, 50 indicate the flow of the salt melt.

EXAMPLES

Catalysts used in the examples described below where prepared as follows:

Catalyst I:

50 kg steatite (magnesium silicate)-rings having an outer diameter of 8 mm, a length of 6 mm and a wall thickness of 1.5 mm were heated to 160° C. in a coating pan and spray-coated with a suspension of 28.6 kg anatase having a BET surface of 20 m$^2$/g, 2.19 kg vanadyl oxalate, 0.176 kg cesium sulphate, 44.1 kg water and 9.14 kg formamide until the weight of the applied coating yielded 10.5% of the total weight of the catalyst (after calcination at 450° C.).

The catalytic coating thus applied, i.e. the catalyst shell, consisted of 4.0 percent by weight vanadium (calculated as $V_2O_5$), 0.4 percent by weight cesium (calculated as Cs) and 95.6 percent by weight titanium dioxide.

Catalyst II:

50 kg steatite (magnesium silicate)-rings having an outer diameter of 8 mm, a length of 6 mm and a wall thickness of 1.5 mm were heated to 160° C. in a coating pan and spray-coated with a suspension of 28.6 kg anatase having a BET surface of 20 m$^2$/g, 4.11 kg vanadyl oxalate, 1.03 kg antimony trioxide, 0.179 kg ammonium dihydrogenphosphate, 0.045 kg cesium sulphate, 44.1 kg water and 9.14 kg formamide until the weight of the applied coating yielded 10.5% of the total weight of the catalyst (after calcination at 450° C.).

The catalytic coating thus applied, i.e. the catalyst shell, consisted of 0.15 percent by weight phosphorus (calculated as P), 7.5 percent vanadium (calculated as $V_2O_5$), 3.2 percent by weight antimony (calculated as $Sb_2O_3$), 0.1 percent by weight cesium (calculated as Cs) and 89.05 percent by weight titanium dioxide.

Example 1

Preparation of PA Using a Reactor According to the Present Invention

A tube bundle having an external diameter of $d_{RBa}$=5.435 m was located in the reactor of the present invention. The tube bundle consisted of about 14,000 catalyst tubes made of steel which each had a length of 3.5 m and an external diameter $d_a$ was thus 1.3793. 4 standard m$^3$/h of air having a loading of 98.5% purity by weight o-xylene of 90 g/standard m$^3$ were passed through the tube from the top downward. The catalyst tubes were filled in a manner to provide for two catalyst zones with different activity. Firstly, catalyst II was filled into each tube to a total height of (as measured from the bottom of the tubes) of 1.3 m. Then a total 1.7 m catalyst I was filled into each tube on top of the catalyst II layer.

The heat transfer medium used was a salt melt of $KNO_3$, $NaNO_2$ and $NaNO_3$ which was passed through the reactor at 348.9° C. and a flow rate of 11,000 m$^3$ per hour. The exit temperature of the melt was 351.1° C. The hot spot temperature of the salt melt was 3.98° C. above the salt inflow temperature.

A plurality of temperature sensors were arranged radially over the cross section at various levels. The temperature differences measured over the reactor cross section were not more than about 2.2° C.

The yield of PA was 78.9 mol %.

Example 2

Comparative Example

Preparation of PA Using a Reactor According to the Prior Art

A tube bundle having an external diameter of $d_{RBa}$=5.021 m was located in the reactor of the prior art. The tube bundle consisted of about 14,000 catalyst tubes made of steel which each had a length of 3.5 m and an external diameter $d_a$=30 mm. The tube spacing t was 38 mm; the ratio t/$d_a$ was thus 1.267. Again, filling of the catalyst tubes—as described in example 1—provided for two zones with different catalyst activity.

4 standard m$^3$/h of air having a loading of 98.5% purity by weight o-xylene of 90 g/standard m$^3$ were again passed through the tube from the top downward. The heat transfer medium used was a salt melt of $KNO_3$, $NaNO_2$ and $NaNO_3$ as in the example according to the present invention.

The inflow temperature of the melt was 345.9° C.; 6200 m$^3$ of melt per hour were passed through the reactor. The exit temperature of the melt was 349.7° C. The hot spot temperature of the salt melt was 7.2° C. above the salt inflow temperature.

The measured temperature differences over the reactor cross section were not more than about 4.2° C.

The yield of PA was 77.8 mol %.

We claim:

1. A multitube reactor which has a catalyst tube bundle comprising numerous parallel catalyst tubes arranged within an outer wall, said catalyst tube bundle having from 10,000 to 50,000 catalyst tubes, and having means for introducing and discharging a heat transfer medium, said means being adapted such that the heat transfer medium is essentially conveyed radially or transversely around the catalyst tubes, wherein the ratio $t/d_a$ of tube spacing t to the external diameter $d_a$ of a catalyst tube is in the range from 1.3 to 1.6, wherein the ratio $t/d_a$ of tube spacing $t$ to the external diameter $d_a$ of a catalyst tube rises with increasing transverse dimensions of the catalyst tube bundle.

2. A multitube reactor as claimed in claim 1, wherein the catalyst tube bundle has an essentially circular cross section having an external diameter $d_{RBa}$ of more than 4 m.

3. A multitube reactor as claimed in claim 2, wherein the external diameter $d_{RBa}$ of the catalyst tube bundle is from 4 m to 12 m.

4. A multitube reactor as claimed in claim 3, wherein the external diameter $d_{RBa}$ of the catalyst tube bundle is from 4 m to 10 m and the ratio $t/d_a$ of tube spacing t to the external diameter $d_a$ of a catalyst tube is in the range from 1.3 to 1.5.

5. A multitube reactor as claimed in claim 1, wherein the catalyst tube bundle has an essentially rectangular cross section with a tube bundle depth $d_{RBt}$ measured parallel to the flow direction of the heat transfer medium of at least 1.3 m.

6. A multitube reactor as claimed in claim in claim 5, wherein the depth $d_{RBt}$ of the catalyst tube bundle is from 1.3 to 4 m.

7. A multitube reactor as claimed in claim 1, wherein the reactor is divided, in the longitudinal direction of the catalyst tubes, into at least two zones, with a flow of heat transfer medium of different temperature being provided in each zone.

8. A multitube reactor as claimed in claim 1, wherein said means for introducing and discharging a heat transfer medium are adapted so as to direct the heat transfer medium in a meandering path.

9. A multitube reactor as claimed in claim 1, wherein said catalyst tube bundle has from 10,000 to 30,000 catalyst tubes.

10. A multitube reactor as claimed in claim 1, wherein said transverse dimensions of the catalyst tube bundle has an external diameter $d_{RBa}$, and wherein the ratio $t/d_a$ rises in a range from 1.3 to 1.6 with the external diameter $d_{RBa}$ of the catalyst tube bundle increasing from 4 m to 12 m for a catalyst tube bundle having an essentially circular cross section or a tube bundle depth $d_{RBt}$ measured parallel to a flow direction of the heat transfer medium increasing from 1.3 m to 4 m for a catalyst bundle having an essentially rectangular cross section.

11. A multitube reactor which has a catalyst tube bundle comprising numerous parallel catalyst tubes arranged within an outer wall, said catalyst tube bundle having from 10,000 to 50,000 catalyst tubes, and having means for introducing and discharging a heat transfer medium; said means being adapted such that the heat transfer medium is essentially conveyed radially or transversely around the catalyst tubes, wherein the ratio $t/d_a$ of tube spacing t to the external diameter $d_a$ of a catalyst tube is in the range from 1.3 to 1.6, wherein the ratio $t/d_a$ of tube spacing t to the external diameter $d_a$ of a catalyst tube rises in a range of from 1.3 to 1.6 with an external diameter $d_{Rba}$ of the catalyst tube bundle increasing from 4 m to 12 m for a catalyst tube bundle having an essentially circular cross section or a tube bundle depth $d_{RBt}$ measured parallel to a flow direction of the heat transfer medium increasing from 1.3 m to 4 m for a catalyst bundle having an essentially rectangular cross section.

* * * * *